(12) United States Patent
Bentley et al.

(10) Patent No.: US 8,183,859 B2
(45) Date of Patent: May 22, 2012

(54) APPARATUS AND METHOD FOR CALIBRATING A TRAMP METAL DETECTOR

(75) Inventors: Brandon Lee Bentley, Amelia, OH (US); Jeffery Shane Lippert, Mount Olivet, KY (US)

(73) Assignee: Carmeuse Lime, Inc., Pittsburgh, PA (US)

( * ) Notice: Subject to any disclaimer, the term of this patent is extended or adjusted under 35 U.S.C. 154(b) by 257 days.

(21) Appl. No.: 12/484,347

(22) Filed: Jun. 15, 2009

(65) Prior Publication Data

US 2010/0315068 A1    Dec. 16, 2010

(51) Int. Cl.
*G01N 27/72*    (2006.01)
(52) U.S. Cl. ........ 324/228; 324/239; 324/326; 324/202; 702/35
(58) Field of Classification Search .................. 324/228, 324/202, 236, 243, 234, 67, 326–329; 340/551; 702/35; 342/22
See application file for complete search history.

(56) References Cited

U.S. PATENT DOCUMENTS

| | | | | |
|---|---|---|---|---|
| 4,084,135 | A |  | 4/1978 | Enabnit .......................... 324/202 |
| 4,672,837 | A |  | 6/1987 | Cottrell, Jr. .......................... 71/1 |
| 4,726,434 | A | * | 2/1988 | Mosher ....................... 177/25.18 |
| 4,805,385 | A | * | 2/1989 | Bohman et al. .............. 56/10.2 J |
| 4,897,015 | A | * | 1/1990 | Abbe et al. .................. 414/744.8 |
| 5,090,574 | A |  | 2/1992 | Hamby ........................... 209/552 |
| 5,160,885 | A |  | 11/1992 | Hannam et al. ............... 324/202 |
| 6,377,872 | B1 | * | 4/2002 | Struckman ..................... 700/258 |
| 6,609,451 | B1 | * | 8/2003 | Inoue et al. ..................... 89/1.13 |
| 6,669,000 | B2 |  | 12/2003 | Wilson et al. ................. 198/367 |
| 6,816,794 | B2 | * | 11/2004 | Alvi ................................ 702/35 |
| 7,658,291 | B2 | * | 2/2010 | Valerio .......................... 209/559 |

* cited by examiner

*Primary Examiner* — Son Le
(74) *Attorney, Agent, or Firm* — Kratz, Quintos & Hanson, LLP

(57) ABSTRACT

An apparatus for calibrating a metal detecting device of a materials processing line. A placement arm is provided to control the path of a calibrating sample in order to simulate movement of tramp metal moving on a processing line along with materials being processed. Upper and lower arms of the placement arm are joined by an adjustable elbow which can be set to a maximum angle of extension in order to accurately place the calibrating sample at a preferred location in a detecting field of the metal detecting device.

7 Claims, 3 Drawing Sheets

APPARATUS AND METHOD FOR CALIBRATING A TRAMP METAL DETECTOR

FIELD OF THE INVENTION

The present invention is an apparatus for use in accurately and efficiently calibrating a tramp metal detector of a materials conveying machine.

BACKGROUND OF THE INVENTION

The term "tramp metal" is used to refer to any metal which is present with a material being processed, which should not be present. It can enter the material stream with the material from an outside source or come from components of the machinery carrying out the procedure.

The presence of tramp metal in materials being processed can cause problems both to the composition of the processed material and to equipment being used in the processing. Therefore, it is known to provide tramp metal detectors at one or more locations along a processing line to detect any tramp metal, in order that action can be taken to remove it from the material stream. A convenient location for installing a tramp metal detector is along a conveying machine, for example a conveying belt, on which the material being processed is loaded.

For materials being processed, which are non-metallic, a metal detector utilizing a magnetic field is typically provided. The material being processed passes through the magnetic field and any disturbance to the field can be detected. Non-metallic material passing through the field may result in a slight disturbance of the field, however, if tramp metal or the like passes through the field a significant and detectable disturbance should result. However, in order for the detecting system to be reliable and in order that nuisance false detections do no occur, it is necessary to maintain the detecting equipment in a well calibrated state.

Processing equipment on which the present invention is beneficial is often located outdoors, is subject to the elements and is often subject to dust, heat etc. which often makes maintaining the calibrated state difficult. Calibration of the equipment may have to be carried out frequently in order to enable safe and efficient operation of the processing line.

Detecting equipment, as described above, is most accurately calibrated by inserting at least one sample, which is representative of metal most likely to be detected, into the magnetic field at a location at which tramp metal would most likely pass if contained in the material being processed. Therefore, calibrating is best performed by discontinuing loading of material on the belt, in order that the pertinent area in the magnetic field is free of the material being processed. This procedure is preferred in order that the sample material of the calibrating device can be placed in the best location for calibrating. Since a discontinuation in loading results in a decrease in production, it is desirable to carry out the calibrating operation in as short a time as possible, but without sacrificing accuracy.

Therefore, there is a need for a device and a method for quickly and accurately calibrating a tramp metal detector on a materials processing line.

OBJECTS OF THE INVENTION

It is an object of the present invention to provide apparatus and method for locating at least one calibrating sample at a previously selected location in a magnetic detecting field in a quick, efficient and accurate manner.

It is also an object of the present invention to maintain the calibrating sample at the selected location for a given period of time in order to carry out the calibrating.

It is still another object of the present invention to locate components of the calibrating apparatus at locations which do not interfere with operation of the conveying equipment when calibrating is not being carried out.

SUMMARY OF THE INVENTION

The present invention is an apparatus for calibrating a metal detecting device of a materials processing line, having a metal detecting field through which materials being processed are passed. The apparatus has a calibrating sample whose presence causes a detectable change of the metal detecting field, and a placement means for temporarily placing the calibrating sample at a selected location in the detecting field when calibrating the metal detecting device.

DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
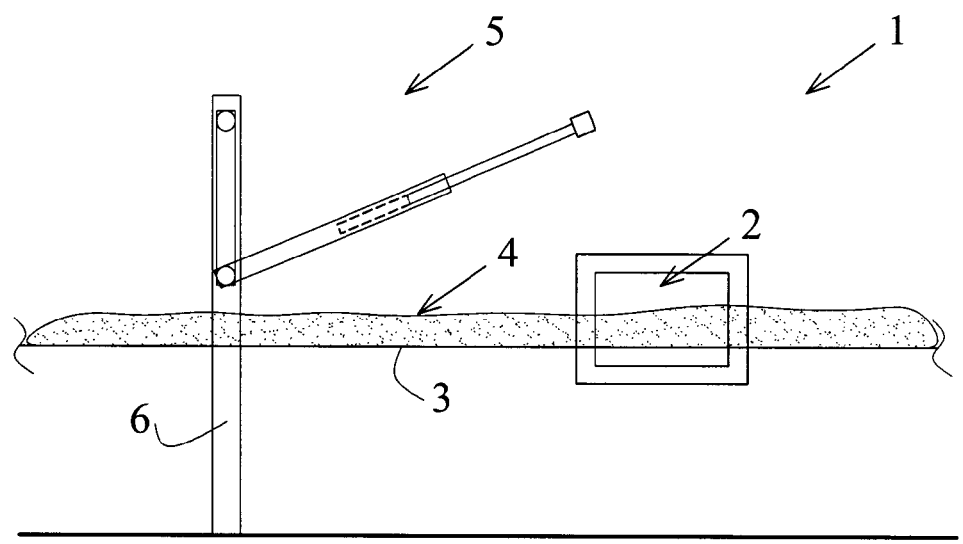
FIG. 1 is a side view of a materials conveying machine having material passing through a detecting field of a tramp metal detecting device.
Figure 2:
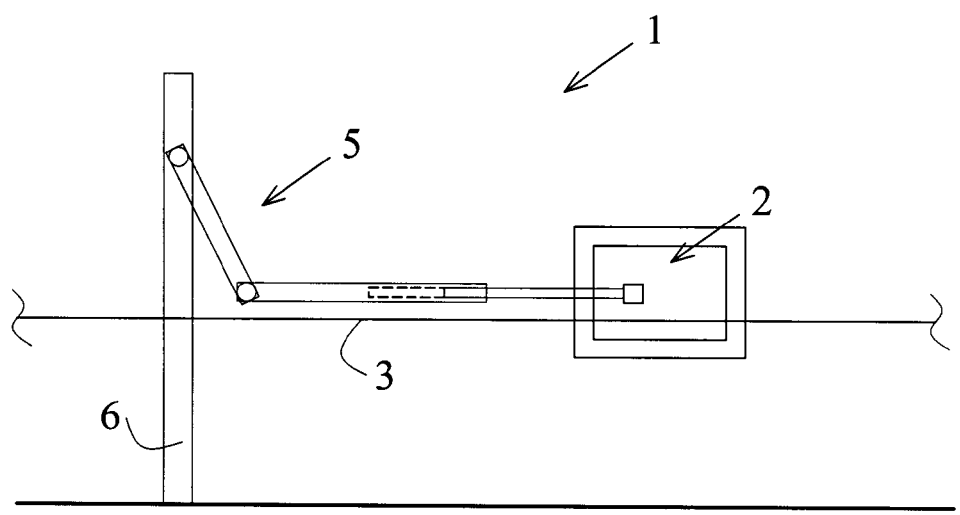
FIG. 2 is a side view of the materials conveying machine of FIG. 1, absent material for processing.

The present invention is preferably mounted on conveying equipment 1, as shown in FIGS. 1 and 2, however practice of the invention is not limited to such a location. In FIG. 1, area 2 denotes an area above a conveying belt 3 at which a magnetic field is provided, and through which material 4, being conveyed to be processed, is passed. FIG. 2 depicts the same conveying equipment 1, found in FIG. 1, however it is shown absent any material, as would be the case when the apparatus of the invention is actually being used for a calibrating operation.

In FIGS. 1 and 2 some components of the apparatus of the invention are indicated at 5, in order to show one possible arrangement of the apparatus in relation to the magnetic field area 2. The apparatus is preferably mounted with use of a framework 6 which is firmly mounted to the conveying equipment, or to the floor or slab supporting the conveying equipment.

Figure 7:
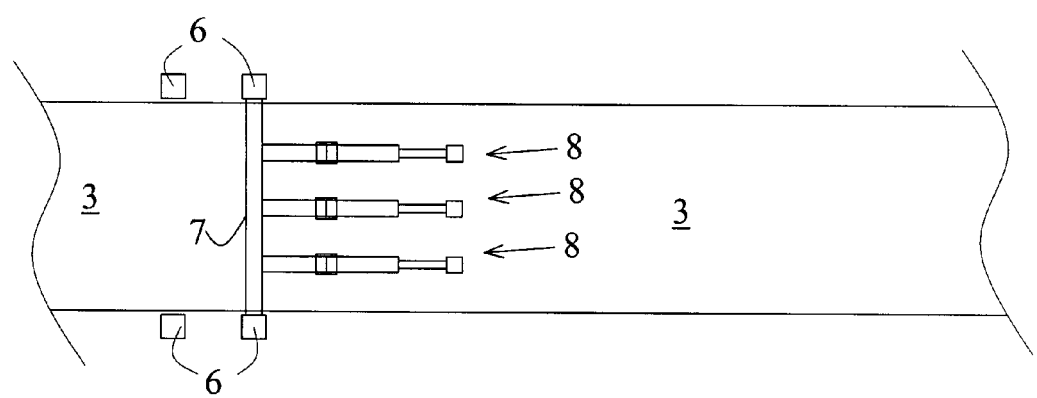
FIG. 7 is a top view of the apparatus of the invention arranged to have a plurality of units.

Further description of the apparatus of the invention is found below, with reference being made to FIGS. 3-7, which provide side and top views of the apparatus. A support shaft 7 extending across a conveying surface of the conveying equipment 1, is mounted to framework 6. The support shaft 7 rotatably supports at least one placement arm 8 having a calibrating sample 9 at an effective end 10 thereof. In order that the placement arm itself does not significantly affect the magnetic field, it is important that the arm be fabricated of a material such as plastic, and the calibrating sample 9 attached to the effective end 10. Although only one placement arm is presently described, any number of placement arms, for example 3 as shown in FIG. 7, can be located across the width of the longitudinal conveyor belt. When more than one placement arm is provided, it is preferable that each be independently operable, although they can all be operated in a similar manner together.

In a preferred embodiment, the placement arm is made up of an upper arm 11, a lower arm 12 and a lower arm extension 13. An adjustable elbow 14 connects the lower arm to the upper arm so as to be hingedly connected and an allowable angle of motion, between the upper arm 11 and the lower arm 12, is adjustable. The lower arm extension 13 is slidingly connected to the lower arm 12 and effectively extends the length of the lower arm 12. The calibrating sample 9 is held at the effective end 10 of the lower arm extension. that is the end which is not slidingly connected to the lower arm 12. The upper arm 11 is hingedly rotatable on the support shaft 7.

Figure 5:
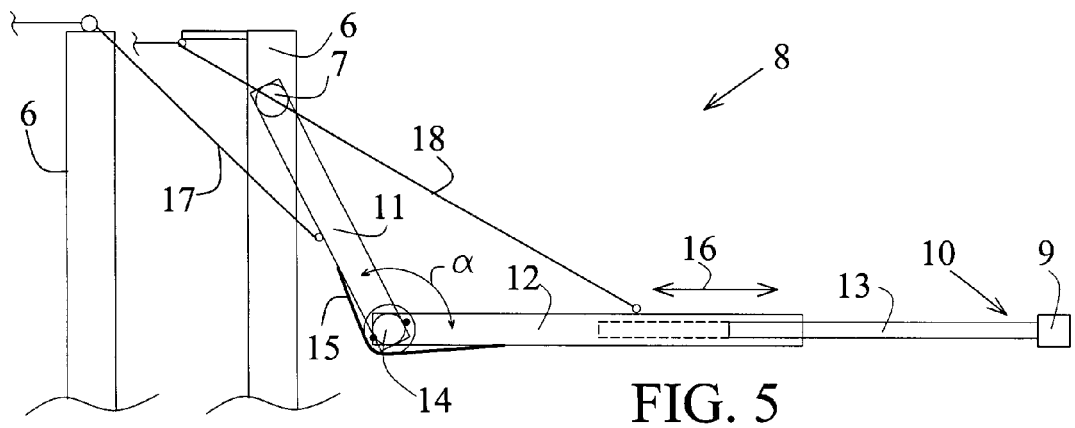
Figure 6:
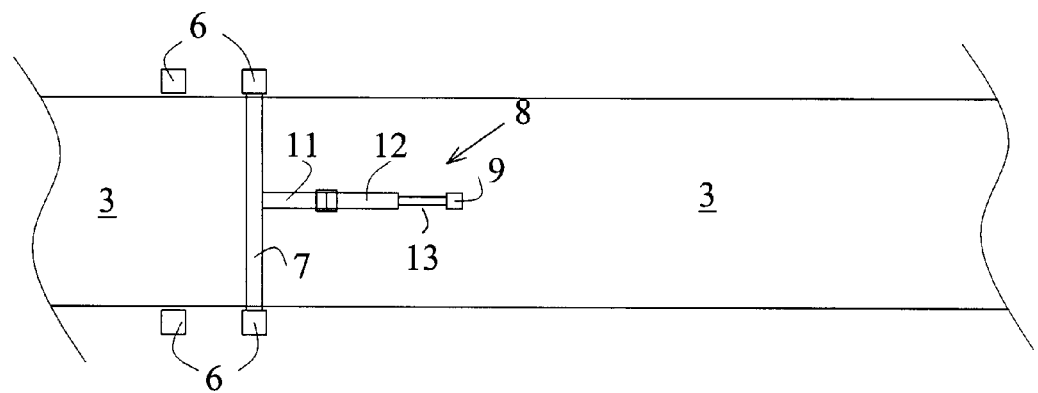
FIG. 6 is a top view of the apparatus of the invention.

As mentioned, the adjustable elbow 14 connects upper arm 11 and lower arm 12 in a hinged manner. Still further, the adjustable elbow 14 limits the angular relationship of the upper and lower arms to a limiting angle $\alpha$, as shown in FIG. 5. Adjustment of the limiting angle, in part, determines the height of the calibrating sample 9 above the conveyor belt 3. The limiting angle is adjustable, but is preferably only done when the calibrating device is initially set up or when a change in the location of the calibrating sample is desired.

Figure 3:
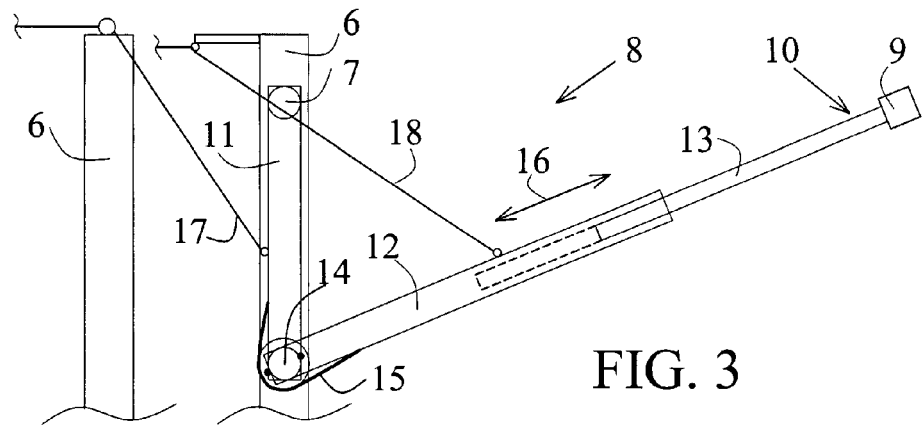
FIGS. 3, 4 and 5 are side views of the apparatus of the invention in various dispositions.
Figure 4:
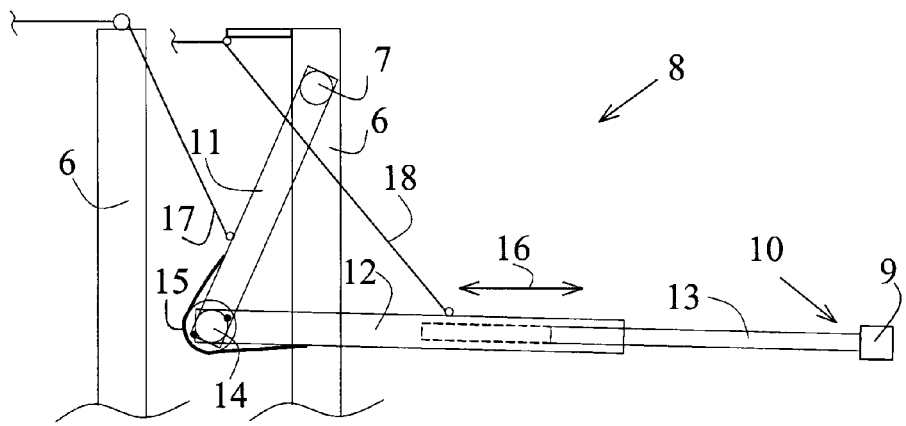

Included with the upper and lower arms and the adjustable elbow is a means to bias the upper and lower arms toward the limiting angle $\alpha$. One means for biasing the upper and lower arms is an elastic cord 15 which extends along an outer portion of the upper and lower arms and around an outer portion of the adjustable elbow, as shown in FIGS. 3-5. Other means include an elongated spring disposed in the same manner as the elastic cord 15, or a spring drum joint or the like. The biasing means facilitates extension of the arms, and the elastic cord accomplishes the extension in a simple manner, without the use of hydraulics or other more complex systems.

In operating the apparatus of the invention, the calibrating sample must be moved from a location at which it does not interfere during normal processing operations with the material being processed, to a location at which it is located at selected locations in the magnetic field, in the area where the material being processed normally is conveyed.

In a preferred embodiment of the invention pulleys and cords are used to position the calibrating sample, however, in practice of the invention hydraulically operated arms, or the like, can be used for operation.

FIG. 3 shows the apparatus of the invention disposed in a non-calibrating disposition. In this disposition the calibrating sample is positioned out of the detecting magnetic field 2. As shown in FIGS. 3-5 the entire placement arm 8 is hingedly rotatable about support shaft 7. Elbow 14 rotatably connects upper arm 11 to lower arm 12 in a hinged manner, however the rotation is limited by the elbow 14 to be less than or equal to the angle $\alpha$ shown in FIG. 5. The value of angle $\alpha$ is adjustable and is adjusted when the apparatus is initially set up so as to precisely locate the calibrating sample at the selected location for best calibrating the tramp metal detector. Also, the lower arm extension 13 is slidably adjustable in lower arm 12 as another adjustment for precisely locating the calibrating sample. The directions for slidably adjusting the lower arm extension 13 are shown in FIGS. 3-5, at 16. Setting the angle $\alpha$ and the location of the lower arm extension 13 in lower arm 12 is carried out substantially only when setting up the calibrating apparatus or changing the location desired for the calibrating sample. It is normally not necessary to change these settings when doing a calibrating procedure, thus time for calibrating is kept to a minimum.

As shown in FIG. 4 the placement arm 8 is at an intermediate stage wherein the upper arm 11 is rotated clockwise on the support shaft 7 to allow the effective end of the lower arm extension and the attached calibrating sample 9 to drop to a position for entering the magnetic field area 2.

In a next step, as shown in FIG. 5, the upper arm 11 is rotated counter clockwise so as to insert the calibrating sample into the magnetic field area 2. The elbow 14 allows the lower arm 12 to drop, so as to be at the angle $\alpha$ in relation to upper arm 11. By having the angle $\alpha$ of the elbow and the lower arm extension 13 properly adjusted, prior to carrying out the calibrating procedure, the calibrating sample is properly positioned in an accurate manner by the above procedure. With use of cord 17, entry of the calibrating sample into the magnetic field area 2, can simulate entry of tramp metal into the magnetic field as it might enter with the material being processed on the moving belt. In a preferred embodiment movement of the calibrating sample is substantially parallel with the belt of the conveyor.

In order to facilitate the above described movements and to hold the upper arm 11 and lower arm 12 at the desired arrangements, cords are preferably used for carrying out the above-described movements. As shown in FIGS. 3-5 cords 17 and 18 are attached to placement arm 8 at various locations and the cords are routed to an area conveniently located for operating by an operator of the line. Grips can be attached to ends of the cords for easier operation.

As shown in FIGS. 3-5, cord 17 is attached to the upper arm 11 and cord 18 is attached to the lower arm 12. With use of cord 17 the placement arms can be moved outwardly away from the magnetic field area 2, and with use of cord 18 lower arm 12 can be moved in an upward direction. Cord 18 works against the biasing force found in adjustable elbow 14. Although cords are used for manipulating the arms of the apparatus, it is possible in practice of the invention to manipulate the arms using hydraulic, electromechanical or other like means.

While specific materials, components, etc. have been set forth for purposes of describing embodiments of the invention, various modifications can be resorted to, in light of the above teachings, without departing from Applicants' novel contributions. Therefore, in determining the scope of the present invention, reference shall be made to the appended claims.

The invention claimed is:

1. An apparatus for calibrating a metal detecting device of a materials processing line, having a detecting field through which materials being processed are passed by a conveyor, comprising:
    a calibrating sample whose presence causes a detectable change of the detecting field, and
    at least one placement means for temporarily placing the calibrating sample at previously selected locations in the detecting field for calibrating the metal detecting device, wherein the placement means:
    holds the calibrating sample to control a path of movement of the calibrating sample to simulate movement of tramp metal moving on the processing line along with materials being processed, and
    continues to hold the calibrating sample to move it away from the detecting field following calibrating the metal detecting device, wherein
    movement of the calibrating sample is independent of movement of the conveyor.

2. The apparatus of claim 1, wherein the placement means comprises a placement arm hingedly rotatable about one end thereof for placing the calibrating sample at the selected locations.

3. An apparatus for calibrating a metal detecting device of a materials processing line, having a detecting field through which materials being processed are passed, comprising:
- a calibrating sample whose presence causes a detectable change of the detecting field, and
- at least one placement means for temporarily placing the calibrating sample at previously selected locations in the detecting field for calibrating the metal detecting device, wherein the placement means holds the calibrating sample to control the path of the calibrating sample to simulate movement of tramp metal moving on the processing line along with materials being processed, wherein
- the placement means comprises a placement arm hingedly rotatable about one end thereof for placing the calibrating sample at the selected locations, and
- the placement arm comprises: an upper arm, a lower arm and an adjustable elbow, wherein the upper arm and lower arm are hingedly connected at elbow ends thereof, the other end of the upper arm being hingedly rotatable from a stationary frame, and the other end of the lower arm holding the calibrating sample.

4. The apparatus of claim 3, wherein the lower arm includes a lower arm extension extendable and contractable in a direction of its length, and the adjustable elbow includes a limiting means for limiting the maximum angle of rotation between the upper arm and the lower arm and a biasing means for biasing the upper arm and the lower arm toward the maximum angle.

5. The apparatus of claim 4, further comprising operating means for remotely rotating the hingedly rotatable end of the upper arm and remotely rotating the upper arm and lower arm at their elbow ends.

6. The apparatus of claim 5, wherein the operating means comprises pulleys and cords.

7. An apparatus for calibrating a metal detecting device of a materials processing line, having a detecting field through which materials being processed are passed, comprising:
- a calibrating sample whose presence causes a detectable change of the detecting field, and
- at least one placement means for temporarily placing the calibrating sample at previously selected locations in the detecting field for calibrating the metal detecting device, wherein the placement means holds the calibrating sample to control the path of the calibrating sample to simulate movement of tramp metal moving on the processing line along with materials being processed;
- the placement means comprises a placement arm hingedly rotatable about one end thereof for placing the calibrating sample at the selected locations; and wherein the placement arm comprises: an upper arm, a lower arm and an adjustable elbow, wherein the upper arm and lower arm are hingedly connected at elbow ends thereof, the other end of the upper arm being hingedly rotatable from a stationary frame, and the other end of the lower arm holding the calibrating sample.

* * * * *